United States Patent
Otis et al.

(10) Patent No.: US 8,261,067 B2
(45) Date of Patent: Sep. 4, 2012

(54) DEVICES, METHODS, AND SYSTEMS FOR SENDING AND RECEIVING CASE STUDY FILES

(75) Inventors: Jason Otis, Monument, CO (US); Jeffrey P. Brokalis, Stephentown, NY (US)

(73) Assignee: Asteris, Inc., Monument, CO (US)

( * ) Notice: Subject to any disclaimer, the term of this patent is extended or adjusted under 35 U.S.C. 154(b) by 990 days.

(21) Appl. No.: 12/221,819

(22) Filed: Aug. 7, 2008

(65) Prior Publication Data

US 2010/0037049 A1 Feb. 11, 2010

(51) Int. Cl.
*H04L 29/06* (2006.01)
(52) U.S. Cl. ............ 713/165; 713/164; 713/168; 705/2; 705/3; 705/50; 705/51; 705/52; 705/67
(58) Field of Classification Search .................. 713/164, 713/165, 168; 705/2, 3, 50, 51, 52, 67
See application file for complete search history.

(56) References Cited

U.S. PATENT DOCUMENTS

| | | | |
|---|---|---|---|
| 5,809,145 A * | 9/1998 | Slik et al. .......................... 705/52 |
| 6,105,134 A * | 8/2000 | Pinder et al. ................... 713/170 |
| 6,137,527 A * | 10/2000 | Abdel-Malek et al. ......... 348/77 |
| 6,275,588 B1 * | 8/2001 | Videcrantz et al. ........... 380/255 |
| 6,578,002 B1 | 6/2003 | Derzay et al. |
| 6,598,011 B1 | 7/2003 | Koritzinsky et al. |
| 6,820,100 B2 | 11/2004 | Funahashi |
| 6,873,435 B1 * | 3/2005 | Tehranchi et al. ............. 358/1.9 |
| 6,901,371 B1 | 5/2005 | Koritzinsky et al. |
| 6,948,069 B1 * | 9/2005 | Teppler ......................... 713/178 |
| 6,988,074 B2 | 1/2006 | Koritzinsky et al. |
| 7,010,144 B1 * | 3/2006 | Davis et al. ................... 382/100 |
| 7,016,952 B2 | 3/2006 | Mullen et al. |
| 7,028,182 B1 * | 4/2006 | Killcommons ............... 713/161 |
| 7,082,440 B2 * | 7/2006 | Ogino et al. ........................ 1/1 |
| 7,266,682 B2 * | 9/2007 | Euchner ........................ 713/152 |
| 7,374,080 B2 * | 5/2008 | Castillo et al. ................ 235/380 |
| 7,493,489 B2 * | 2/2009 | de Queiroz ................... 713/176 |
| 7,688,995 B2 * | 3/2010 | Stoeckel ........................ 382/100 |
| 7,698,230 B1 * | 4/2010 | Brown et al. .................... 705/75 |
| 7,774,605 B2 * | 8/2010 | Kanai et al. ................... 713/176 |
| 7,882,177 B2 * | 2/2011 | Wei et al. ...................... 709/204 |
| 8,121,342 B2 * | 2/2012 | Davis et al. ................... 382/100 |
| 2002/0016718 A1 * | 2/2002 | Rothschild et al. ............... 705/2 |
| 2002/0016922 A1 | 2/2002 | Richards et al. |

(Continued)

FOREIGN PATENT DOCUMENTS

WO   WO 02/09357 A2   1/2002

OTHER PUBLICATIONS

Digital Imaging and Communications in Medicine, DICOM Standard, 2001. Retrieved from http://medical.nema.org/ on May 10, 2011.*

*Primary Examiner* — April Shan
(74) *Attorney, Agent, or Firm* — Brooks, Cameron & Huebsch PLLC.

(57) ABSTRACT

The present disclosure includes devices, methods, and systems for creating a case study file that includes an image file from an imaging modality, executing a hash algorithm on the case study file to produce a hash key, compressing the case study file, bundling the hash key with the compressed file, encrypting the bundled file, and moving the encrypted bundled file through an Internet connection to a storage computing system, among other embodiments.

40 Claims, 5 Drawing Sheets

U.S. PATENT DOCUMENTS

| | | | |
|---|---|---|---|
| 2003/0140044 A1* | 7/2003 | Mok et al. | 707/10 |
| 2004/0015441 A1* | 1/2004 | Ebihara et al. | 705/50 |
| 2004/0022444 A1* | 2/2004 | Rhoads | 382/232 |
| 2004/0146272 A1* | 7/2004 | Kessel et al. | 386/46 |
| 2004/0148503 A1* | 7/2004 | Sidman | 713/167 |
| 2005/0102158 A1* | 5/2005 | Maeda | 705/2 |
| 2005/0114179 A1* | 5/2005 | Brackett et al. | 705/2 |
| 2005/0114380 A1* | 5/2005 | Eldar et al. | 707/102 |
| 2006/0097040 A1* | 5/2006 | Castillo et al. | 235/380 |
| 2006/0136723 A1* | 6/2006 | Taylor | 713/168 |
| 2006/0229911 A1 | 10/2006 | Gropper et al. | |
| 2006/0230072 A1* | 10/2006 | Partovi et al. | 707/104.1 |
| 2007/0005798 A1 | 1/2007 | Gropper et al. | |
| 2007/0027715 A1 | 2/2007 | Gropper et al. | |
| 2007/0124410 A1* | 5/2007 | Hofstetter | 709/217 |
| 2007/0220614 A1* | 9/2007 | Ellis et al. | 726/27 |
| 2008/0021834 A1* | 1/2008 | Holla et al. | 705/51 |
| 2009/0313170 A1* | 12/2009 | Goldner et al. | 705/50 |

* cited by examiner

DEVICES, METHODS, AND SYSTEMS FOR SENDING AND RECEIVING CASE STUDY FILES

BACKGROUND

In many fields (e.g., medicine, manufacturing, veterinary science, scientific research, etc.), it can be useful to examine a subject and communicate the results of the examination to a different location. However, the speed at which the results can be sent to the different location can be quite slow. Mailing the results can take up to three to four days, and transporting the results over an Internet connection can take hours depending on the connection speed and the size of the file. In addition, the use of the Internet connection to download the results can cause other information being sent to be delayed or lost completely.

In many instances, the speed of transmission can be largely affected by the size of the file being sent containing the results. For example, a magnetic resonance imaging (MRI) study on a patient may include text and approximately 100 images, each of which may be 300 to 500 kilobytes (Kb) in size, leading to a study of 50 to 80 megabytes (Mb) total of data. A study of this size, especially if combined with other types of images from different modalities can prove difficult to transport in a timely fashion.

The ability to transfer such information in a timely fashion without data loss to a different location can be further hampered by the issue of keeping the information secure and confidential. Some systems include some form of security measure, such as the use of passwords. Password identification determines whether a user is authorized to gain access to a system. However, passwords can be insufficient mechanisms to maintain patient confidentiality from intruders who gain knowledge of a user's password to log onto a system and "man in the middle" attacks on the Internet. Other systems have employed point-to-point connections between sites and private networks, such as wide area networks (WANs). However, these systems are often inflexible and expensive since they can require customized installation and support for each site.

DETAILED DESCRIPTION

Figure 1:
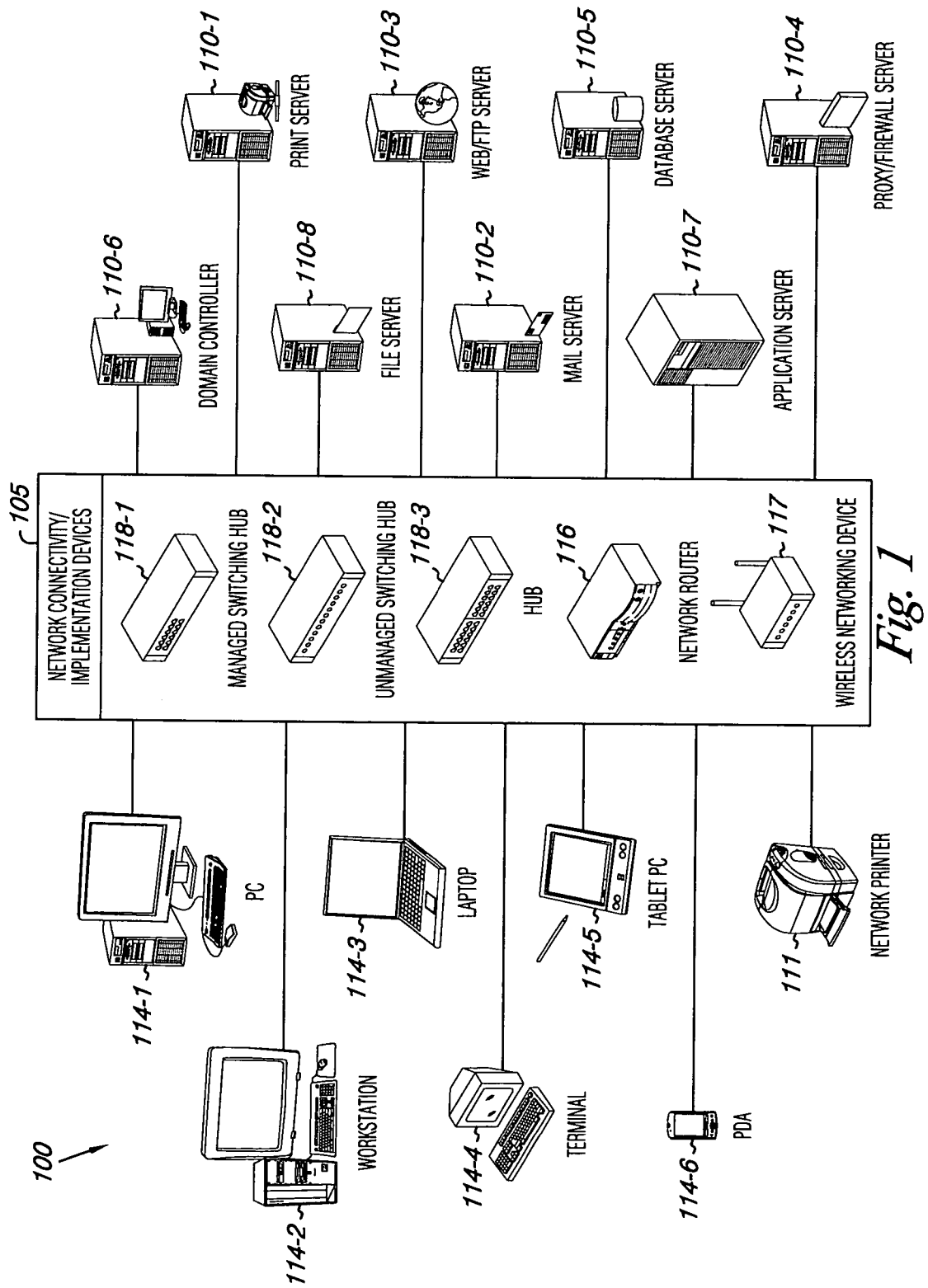
FIG. 1 illustrates a computing device network in which one or more embodiments of the present disclosure can be implemented.

According to the present disclosure, devices, systems, and methods are provided for creating a case study file that includes an image file from an imaging modality, executing a hash algorithm on the case study file to produce a hash key, compressing the case study file, bundling the hash key with the compressed file, encrypting the bundled file, and moving the encrypted bundled file through an Internet connection to a storage computing system, among other embodiments.

As used herein, a "case study file" can include a file containing medical data generated or acquired for medical study, and a "case study" can include a collective grouping of one or more case study files.

As used herein, an "imaging modality" can include radiology equipment grouped as small matrix size and large matrix size instruments. Small matrix size systems include equipment for magnetic resonance imaging (MRI), computed tomography (CT), ultrasonography (US), nuclear medicine (NM), and digital fluorography. Large matrix size systems can include equipment for computer radiography (CR) and digitized radiography (DR). Other imaging modalities may be also used for radiofluoroscopy, angiography, such as x-ray angiography, and heart scanning. Still other imaging modalities useful in acquiring medical information includes secondary capture devices for video, endoscopy, microscopy, and photography, such as digital cameras, scanners, electrocardiogram (ECG) machines, and the like.

The imaging modalities can be used to create the image file, which can be placed into the case study file, as discussed herein. In addition to image files, however, other medical information in numerous forms including text and video, or variations thereof, such as image overlay data, measurements, coordinates, etc. can also be included into the case study file. Information placed in the case study file may also be in the form of time-dependent data including sound, such as audio, dictation, and waveform data. The case study file can also include document files, for example Adobe Portable Document Format (PDF) files, Microsoft Word™ documents, and/or Microsoft Power Point presentations, among others.

In some embodiments, methods of the present disclosure can be carried out by executable instructions stored in memory and executed by a processor in a computing device. The executable instructions can, for example, be included in a computing device readable medium. In such embodiments, a computing device readable medium can be any medium that can store computer readable information thereon. Suitable examples include optically or magnetically readable forms of media, among others.

Embodiments of the present disclosure will now be described in relation to the accompanying drawings, which will at least assist in illustrating the various features of the various embodiments. In the Figures, the first digit of a reference number refers to the Figure in which it is used, while the remaining two digits of the reference number refer to the same or equivalent parts of embodiment(s) of the present disclosure used throughout the several figures of the drawing. The scaling of the figures does not represent precise dimensions and/or dimensional ratios of the various elements illustrated herein.

As used herein, a "network" refers to a communication system that links two or more computers and peripheral devices and allows users to access resources on other computers and exchange messages with other users. A network may provide connections to the Internet. Users may interact with network-enabled software applications to make a network request, such as to take an image on an image modality or print on a network printer. The application may also communicate with the network software, which may then interact with the network hardware to transmit information to other devices attached to the network.

A "local area network" (LAN) is a network that is located in a particular physical area, such as a building, in which computers and other network devices are linked, usually via a wiring-based cabling scheme. A LAN typically includes a shared medium to which workstations attach and through which they communicate. Local area networks often use broadcasting methods for data communication, whereby a device on the LAN can transmit a message that other devices on the LAN then "listen" to. However, the device or devices to which the message is addressed actually receives the message that is transmitted. Data is typically packaged into frames for transmission on the LAN, as will be further described herein.

FIG. 1 illustrates an example of a computing device network 100 in which one or more embodiments of the disclosure can be implemented. As shown in FIG. 1, a number of devices, e.g., personal computers (PCs), servers, imaging modalities, peripherals, etc., can be networked together in a LAN and/or wide area network (WAN) via routers, hubs, switches, and the like. The computing device network 100 shown in FIG. 1, for example, can illustrate a network at a clinic or hospital. As used herein, a "computing device" refers to a switch, router, hub, bridge, etc., i.e., a device having processor and memory resources, as the same will be understood by one of ordinary skill in the art. As the reader will appreciate, the term "computing device" can also be used to refer to servers, PCs, etc., as illustrated further herein. In addition, although the computing device is shown in the network of FIG. 1, in some embodiments, the computing device can be at a remote location with a connection to the Internet, without being networked to other devices as in a LAN.

The example network of FIG. 1 illustrates a number of servers, including a print server 110-1 to handle print jobs for the network 100, a mail server 110-2, a web server 110-3, a proxy server (firewall) 110-4, a database server 110-5, a domain controller 110-6, an application server 110-7, and a file server 110-8. The examples described herein do not provide an exhaustive list of servers that may be used in a network.

The network embodiment of FIG. 1 further illustrates a network printer 111. Other network-capable devices, including one or more additional printers, may be used in a network.

The network embodiment of FIG. 1 further illustrates a number of computing devices, including PC 114-1, workstation 114-2, laptop 114-3, terminal 114-4, tablet PC 114-5, and PDA 114-6. Each computing device is equipped with resources, i.e., processor and memory resources, to perform larger application processing and/or storage. In addition, each computing device 114-1, . . . , 114-N can be connected to one or more imaging modalities, as discussed herein. The examples described herein do not provide an exhaustive list of computing devices that may be used in a network.

The embodiment of FIG. 1 illustrates the example network devices connected to one another and/or to other networks using network connectivity and/or network implementation devices 105, such as router, 116, wireless networking device 117, managed switching hub 118-1, unmanaged switching hub 118-2, and/or hub 118-3. The examples described herein do not provide an exhaustive list of means for connecting the example network devices to one another and/or to other networks. As noted above, such network devices can include a processor in communication with a memory and will include network chips having hardware logic, e.g., in the form of application specific integrated circuits (ASICs), associated with a number of network ports. The term "network" as used herein is not limited to the number and/or type of network devices illustrated in FIG. 1. And, embodiments of the various devices in the network are not limited to a number, type, or size of processor or memory resources and/or logic.

Program instructions (e.g., computer executable instructions), can reside on the various computing devices. For example, program instructions in the form of firmware, and/or software (both in the form of executable instructions) can be resident on the network 100 in the memory of the computing devices 114-1, 114-2, 114-3, 114-4, 114-5, and 114-6, router 116, wireless networking device 117, and/or hubs 118-1, 118-2, and 118-3, and can be executable by the processor(s) and/or logic (e.g., hardware in the form of transistor gates) thereon. Also, program instructions can be resident in a number of locations on various computing devices in the network 100 as can be employed in a distributed computing network.

A "distributed computing network" refers to the use of multiple computing devices, e.g., having processor and memory resources, in a network to execute various roles in executing instructions, e.g., application processing, etc., as described herein. "Software" as used herein, includes a series of executable instructions that can be stored in memory and executed by the hardware logic of a processor (e.g., transistor gates) to perform a particular task. Memory, as the reader will appreciate, can include but is not limited to random access memory (RAM), read only memory (ROM), non-volatile memory (e.g., Flash memory), etcetera.

Figure 2:
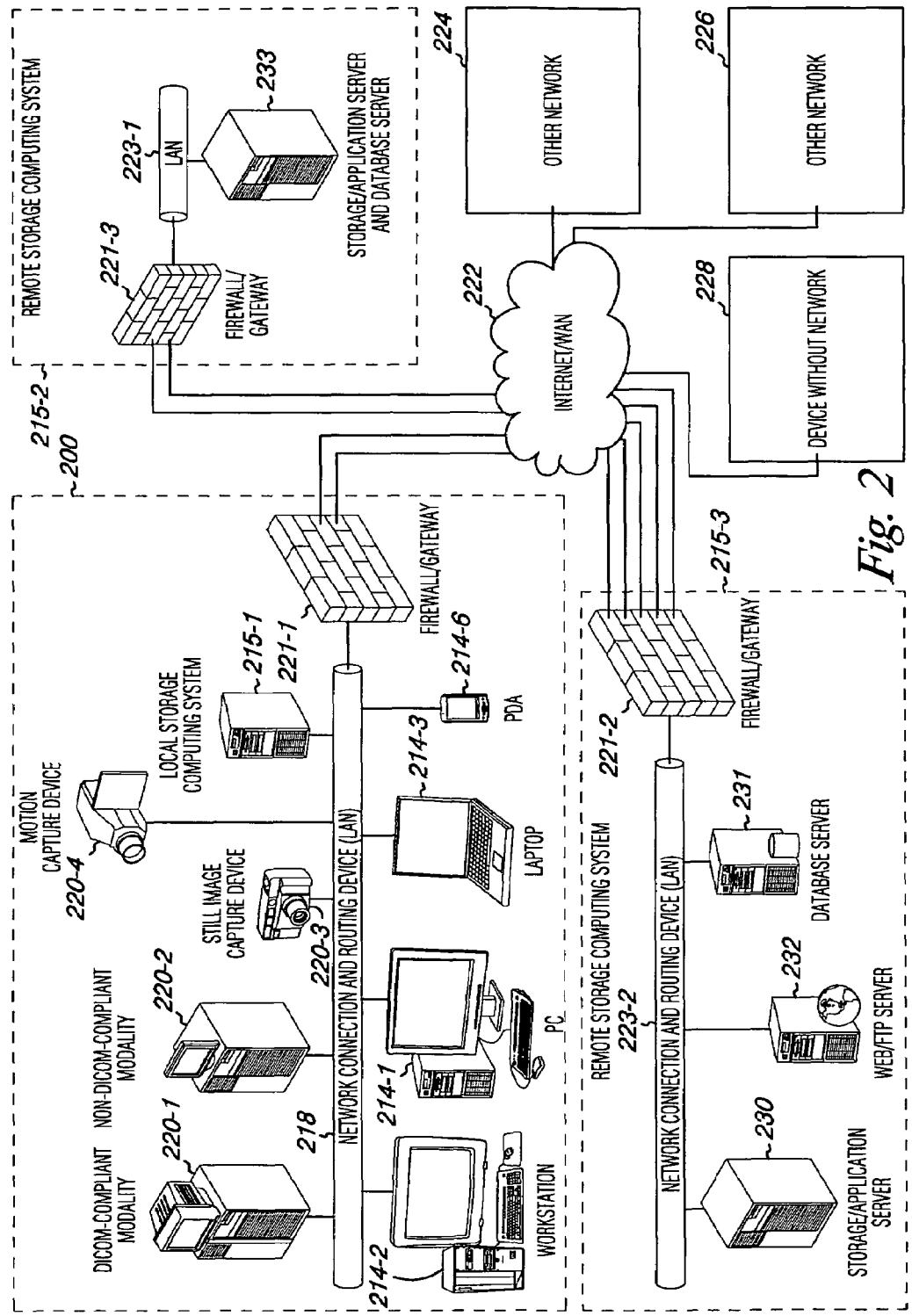
FIG. 2 illustrates a portion of a computing device network in which one or more embodiments of the present disclosure can be implemented.

FIG. 2 illustrates an example of a portion of the network 200 where computing devices 214-1, 214-2, 214-3, and 214-6 are connected to one or more imaging modalities, including DICOM-compliant modality 220-1, non-DICOM-compliant modality 220-2, still image capture device 220-3, and motion capture device 220-4. The examples described herein do not provide an exhaustive list imaging modalities or of computing devices that may be connected to the imaging modalities.

The network 200 is connected to a local storage computing system 215-1 and remote storage computing systems 215-2 and 215-3. Although network 200 is shown connected to two remote storage computing systems, network 200 could be connected to any number of remote storage computing systems, as will be appreciated by one of ordinary skill in the art. Remote storage computing systems 215-2 and 215-3 can include local area networks (LANs) 223-1 and 223-2, storage/application servers 233 and 230, and firewall/gateway 221-3 and 221-2, respectively. Remote storage computing systems 215-2 and 215-3 can also include additional devices, as will be understood by one of ordinary skill in the art. In some embodiments, a local connection could suggest network communications between one or more devices within a local area network (LAN), e.g., LAN 218, of network 200 behind a firewall or network routing device, e.g., firewall/gateway 221-1, while remote connection could suggest network communications between one or more devices within a wide area network (WAN), e.g., internet/WAN 222, where traversal through one or more firewalls, network routing devices or gateways, e.g., firewalls/gateways 221-1 221-2, and 221-3, is required.

On the network 200, diagnostic data acquired by multiple modalities 220-1, 220-2, 220-3, and 220-4 can be handled through each of the computing devices 214-1, 214-2, 214-3, and 214-6. Each of the modalities and each of the computing devices that can electrically accept or process the diagnostic images can be connected to the network 200 using a network interface card (NIC) or any other device that implements the required networking protocols.

As appreciated by those skilled in the art, the modalities 220-1, 220-2, 220-3, and 220-4 can serve as sources of medical data, or digital files, including DICOM-compliant apparatus 220-1, non-DICOM-compliant apparatus 220-2, still image apparatus 220-3, motion capture apparatus 220-4, and other diagnostic or imaging devices (not shown), which could include infrared cameras, thermal translation devices, or any other device or system that produces medical data that can be stored to a memory.

In some instances, each of the imaging modalities 220-1, 220-2, 220-3, and 220-4 can be located in a dedicated diagnostic room in a hospital or clinic. Furthermore, specialized technicians, such as radiographers, can be deployed to each of the modalities to acquire data representative of affected parts and/or entire bodies of patients, inspect the acquired data, and/or possibly re-acquire the affected parts and/or entire body.

In some embodiments, each of the computing devices 214-1, 214-2, 214-3, and 214-6 and modalities 220-1, 220-2, 220-3, and 220-4 can be connected transparently according to a predetermined communication protocol. For example, in the case of open systems interconnection (OSI) reference standard model, a physical layer and data link layer of the network are constructed by the Ethernet, while a transport layer and network layer are constructed by the transmission control protocol/internet protocol (TCP/IP). Upper layers higher than a session layer inclusive can be provided as specialized protocols given by the manufacturers of medical products.

In some embodiments, one of the representative upper layers of protocol can be digital imaging and communication for medicine (DICOM). DICOM is the industrial standard specifying the format and transfer of images and other medical information between computing devices, which allows the digital communication between a diagnostic apparatus and a therapeutic apparatus produced by different manufacturers. As such, the medical data file may be in the DICOM format. Designed to permit the transfer of medical data in a multi-vendor environment, the DICOM standard is defined and regulated by the National Electrical Manufacturers Association (NEMA).

Using the network system for images as shown in FIG. 2, every image acquired in a hospital or clinic can be digitized and thereafter moved, transferred, distributed, or shared among multiple computing devices 214-1, 214-2, 214-3, and 214-6 on the network 200. In other words, diagnostic data obtained in a diagnostic room is also available to a computing device provided in another diagnostic room within the network 200.

As discussed herein, the network 200 and the local storage computing system 215-1 can communicate within a LAN, e.g., LAN 218. The network 200 and the remote storage computer system 224 can communicate over a WAN, which can be in the form of the Internet 222, but may be any communication network. Connections to the Internet 222 might be made by use of a gateway device, e.g., gateway 221-1, which may implement a networking firewall for security.

In some embodiments, a facility may only require the use of a local storage computing system, e.g., local storage computing system 215-1, if there is no need for offsite data storage or remote data access. In other embodiments, a facility may only require the use of a remote storage computing system, e.g., remote storage computing system 215-2. In other embodiments, a facility may implement both local storage computing system 215-1 and remote storage computing system 215-2 to increase security and/or performance for medical data storage and/or retrieval within the LAN, while allowing for offsite data storage and access for computing devices that are not within the LAN. In other embodiments, medical data might be sent to both remote storage computing systems 215-2 and 215-3 to implement alternate and/or redundant storage, retrieval, functionality, and/or performance. In other embodiments, remote storage computing systems 215-2 and 215-3 may send data to or receive data from one another for increased redundancy and/or data synchronization purposes.

The term "storage computing system" is used in a generic sense and is not intended to be limited. Multiple storage computing systems may be used for the purposes of redundancy as a fail-over mechanism to increase reliability, to provide sufficient throughput and resource allocation, and to provide for regional segregation to satisfy, for instance, national regulatory issues, etcetera. The storage computing systems 215-1 and 224 can provide routing for case study files to other clinics, hospitals, and/or other users. In some embodiments, the storage computing systems 215-1 and 224 can also provide archiving, as discussed herein.

In some embodiments, the storage computing systems 215-1, 215-2, and 215-3 may be individually comprised of more than one computing device to divide any required tasks or process allocation between said devices for increased redundancy, performance, and/or security, or for any other reason that might warrant multiple devices. Examples of separate computing devices for this configuration might include storage and application server 230, database server 231, and/or web or internet application server 232.

By including the connection to the Internet 222, the network 200 can be connected to remote storage computing systems 215-2 and/or 215-3, as discussed herein. The remote storage computing systems 215-2 and/or 215-3 can also be connected to other networks, e.g., networks 224 and/or 226, through the Internet 222. In some embodiments, the remote storage computing systems 215-2 and/or 215-3 can be connected to a computing device 228 through the Internet 222, where the computing device 228 is not a part of a network.

As shown, in some embodiments, the primary connection of each network 200, 224, 226, and computing device 228, is to the remote storage computing systems 215-2 and/or 215-3. The various networks 200, 224, 226, and computing device 228, have no direct connection to each other and without the actions and management of the remote storage computing systems 215-2 and/or 215-3, no usable data transfer occurs.

In addition, as shown, an aspect of the system is its "virtual" nature. Institutional networks can be complicated by technical, administrative, legal, and regulatory requirements. Opening up these networks directly to each other can be a complex problem that is normally not attempted. However, methods and systems of the present disclosure use a Push model of data transfer wherein data is pushed to the recipient (e.g., data is pushed from the computing devices, e.g., computing devices 214-1, 214-2, 214-3, 214-6, and 228, to the remote storage computing systems 215-2 and/or 215-3). By using the Push model, technical, administrative, legal, and regulatory involvement can be reduced. In addition, with networks 200, 224, 226 employing firewalls, the Push model can allow the bundled file to be sent to the remote storage computing systems 215-2 and/or 215-3, without alteration of standard firewall rules; only firewall 221-2 at remote storage computing system 215-3 will require a one-time rule modification to allow data from approved sites, users, or applications.

The embodiment illustrated in FIG. 2 is used to perform methods of the present disclosure. The embodiments described herein can be performed by software (as the same has been described herein), hardware in the form of logic, and/or application modules (i.e., a self-contained hardware or software component that interacts with a larger system) on the systems and devices shown herein or otherwise. As the reader will appreciate, a software module may come in the form of a file and handle a specific task within a larger software system. A hardware module may be a separate set of logic (e.g., transistor/circuitry gates) that "plug-in" as a card or otherwise, to a larger system and/or device. Embodiments described herein are not limited to a particular operating environment and/or to software or executable instructions composed in a particular language or syntax.

In some embodiments, the computing devices 214-1, 214-2, 214-3, and 214-6 can be used to create a case study file. In the computing devices 214-1, 214-2, 214-3, and 214-6 of FIG. 2, the computing devices 214-1, 214-2, 214-3, and 214-6 include one or more processors in communication with one or more memory locations. The memory can include a number of executable instructions that can be executed on the processor. Memory can also include one or more items of data that can be used in the execution of the instructions by the processor. The executable instructions can be executed by the processor to cause the computing devices 214-1, 214-2, 214-3, and 214-6 to perform a method of the present disclosure, as described herein.

Figure 3:
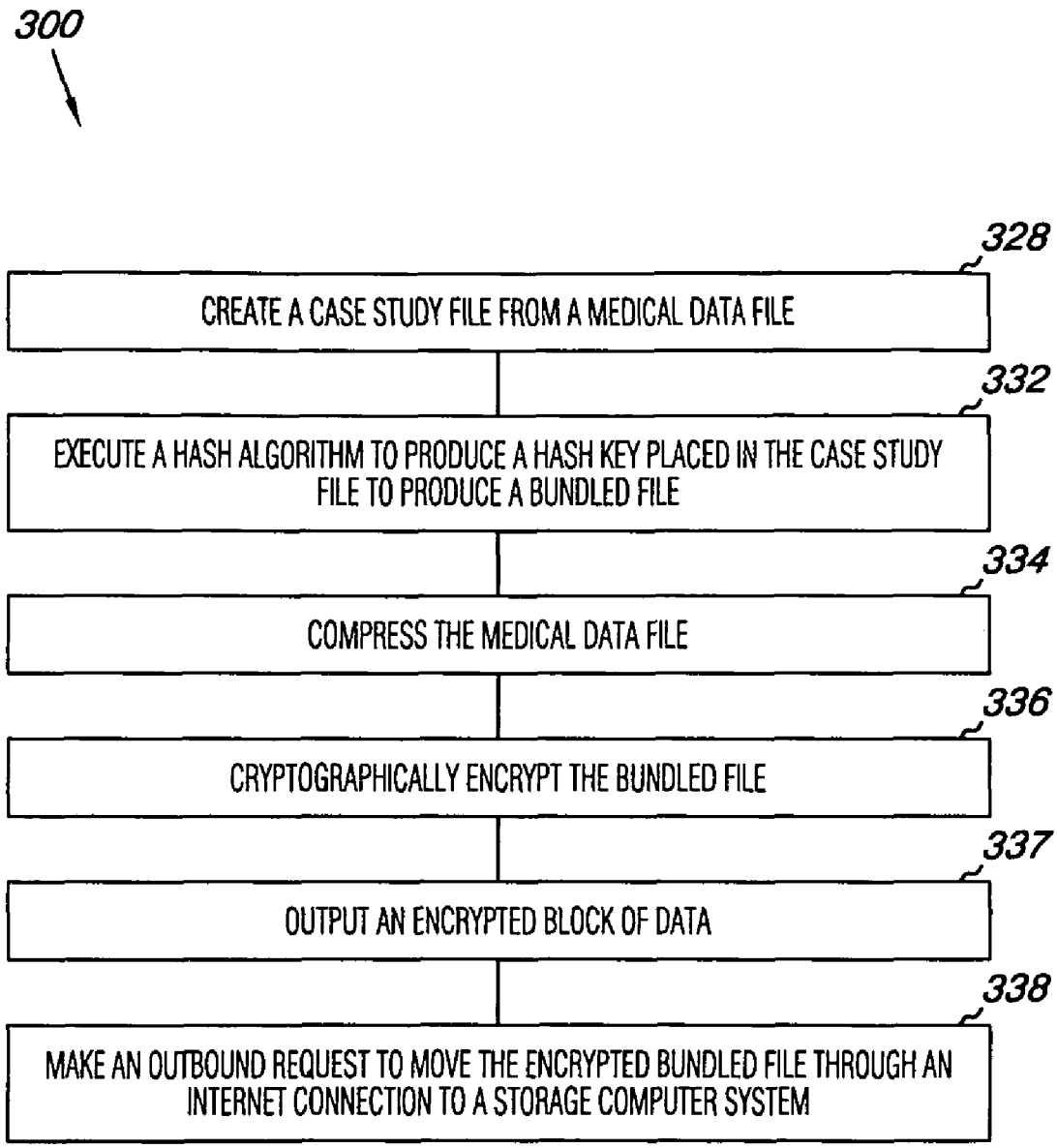
FIG. 3 illustrates a method for creating a case study file in accordance with one or more embodiments of the present disclosure.

FIG. 3 illustrates a method for creating a case study file according to embodiments of the present disclosure. Unless explicitly stated, the method embodiments described herein are not constrained to a particular order or sequence. Additionally, some of the described methods embodiments can occur or be performed at the same point in time. Further, although reference is made to creating a case study file from a medical data file, embodiments of the present disclosure are not so limited, and can include methods for creating case study files from other types of data files. That is, a medical data file is one type of case study file that can be used in accordance with the present disclosure, but embodiments of the present invention are not so limited, and can include other types of case study files.

In some embodiments, methods of the present disclosure can be carried out by executable instructions stored in memory and executed by a processor in a computing device. The executable instructions can also be included in a computing device readable medium. In such embodiments, a computing device readable medium can be any medium that can store computing device readable information thereon. Suitable examples include optically or magnetically readable forms of media and solid state storage devices, among others.

As illustrated at block 328, the method 300 includes creating a case study file from a medical data file. In some embodiments, the medical data file can include an image file from an imaging modality, as discussed herein. The medical data can also be text files, video files, audio files, and wave form data, as well as documents or any other applicable digital format.

As illustrated at block 332, the method 300 includes executing a hash algorithm to produce a hash key placed in the case study file to produce a bundled file. In some embodiments, the hash algorithm can be executed on the entire case study file, not just the medical data file. Executing the hash algorithm includes a method of turning some kind of data (e.g., the medical data file) into a relatively small number that may serve as a digital "fingerprint" of the data contained therein. In some embodiments, the hash algorithm substitutes or transposes the data to create such fingerprints. The hash key is based on a hash value, which is a value that is computed from a base input number using the hash algorithm. Essentially, the hash value is a summary of the original value. It is nearly impossibly to derive the original input number without knowing the data that created the hash value. For example, hash keys can use complex algorithms and very large hash values for encrypting, including 64-bit or even 128-bit numbers. A 128-bit number has a possible $2^{128}$ different combinations.

When the hash key is attached to the case study file, a case study file that is corrupted or impersonated can be detected. For example, when the bundled file is sent over an Internet connection, as discussed herein, the receiving party can perform the hash algorithm again based on the hash key. If the hash value is calculated for a piece of data, and if one bit of that data is changed, the hash algorithm produces a completely different hash value, indicating an error has occurred at some point during the transmission. Exemplary hash algorithms executed can include, but are not limited to Secure Hash Algorithm (SHA)-1, and SHA-2 (i.e., SHA-224, SHA-256, SHA-384, and SHA-512), among others. The SHA has functions are designed by the National Security Agency (NSA) and published by the National Institute of Standards and Technologies (NIST) as a U.S. Federal Information Processing Standard.

At block 334, the medical data file is compressed. Compressing the bundled file can reduce the overall number of bits in the case study file so it can be transmitted, for example, to a receiving device, medium, or across a network, faster than an uncompressed file and it can take less space on a computing device readable medium or in a computing device memory. As appreciated by one skilled in the art, file compression algorithms can reduce the redundancy in a file by listing information once and then referring back to it whenever it appears in the original file.

In some embodiments, the type of compression can be lossless compression. As used herein, "lossless compression" refers to the process of compressing a file in such a way that lets a computing device recreate the original file exactly. Exemplary compression implementations include DEFALTE, LZMA, LZO, and bzip2, among others. By using lossless file compression within the case study file bundling process, files of any format can be reconstructed to their original state without degradation. Lossy image compression algorithms render permanent loss of image data and thus quality. Lossless image compression algorithms can also be utilized, but will typically result in file sizes, e.g., number of bits, greater than those encoded with file compression algorithms. Also, image compression algorithms can not be applied to files that do not contain image data.

At block 336, the bundled file is cryptographically encrypted, including the compressed medical data file and the hash key. Cryptographic encryption can require an encryption key and a cryptographic encryption algorithm. Encryption of the bundled file can provide a level of security for information contained in the case study file that is meant to be kept private. Encryption is a process of encoding information in such a way that only a computing device with the key can decode it.

Symmetric-key encryption is where each computing device has a secret key (e.g., code) that it can use to encrypt a packet of information before it is sent to or referenced by another computing device. Symmetric-key encryption requires that the each computing device is known so that the key can be installed on each one. Respected symmetric-key algorithms include Advanced Encryption Standard (AES), Blowfish, Rivest Cipher 4 (RC4), and Triple Data Encryption Standard (TDES).

Public-key encryption uses a combination of a private key and a public key. The private key is known only to the originating computing device, while the public key is given by the originating computing device to any computing device that wants to communicate securely with the originating computing device. To decode an encrypted file, a computing device can use the public key, provided by the originating computing device, and its own private key.

Since public-key encryption can require significant resources, some systems use a combination of public-key and symmetry. For example, when two computers initiate a secure session, one computing device creates a symmetric key and sends it to the other computer using public-key encryption. Once the session is finished, each computing device discards the symmetric key used for that session.

At block 337, an encrypted block of data is output. The encrypted block of data contains information pertinent to the compression algorithm applied to the original medical data file, the hash key, informational or reference data applicable to the original medical data file, and the compressed file. In some embodiments, additional data regarding the encryption algorithm used and/or other information required to decrypt the encrypted block of data may be added to the file by an output file generator.

As illustrated at block 338, the method 300 includes making an outbound request to move the encrypted bundled file through an internet connection to a storage computing system. As discussed herein with respect to FIG. 2, the computing device can be in a network connected to the storage computing system through the internet. In some embodiments, the bundled file can move to the storage computing system through an unsecure internet connection, since the file is itself encrypted by algorithms similar to those utilized to establish a secured internet connection. As used herein, an "unsecure internet connection" is a connection that is not encrypted and does not require a password or login for use.

As discussed herein and pertinent to DICOM modalities and standards, encrypting the bundled file prior to sending the bundled file to the storage computing system can reduce the need for the installation and maintenance of expensive picture archiving and communication system (PACS). In addition, the use of an unsecure Internet connection can allow more users access to the storage computing system relatively inexpensively and with increased performance, as compared to encrypting an internet connection for the use of bundled file transfer.

In some embodiments, the encrypted bundled file can be transferred through the internet using the internet protocol (IP) suite. The IP suite can be viewed as a set of layers. Each layer solves a set of problems involving the transmission of data, and provides a well-defined service to the upper layer protocols based on using services from some lower layers. Upper layers are logically closer to the user of a computing device and deal with more abstract data, relying on lower layer protocols to translate data into forms that can eventually be physically transmitted.

In some embodiments, the encrypted bundled file can be transferred through the internet using the TCP/IP protocol suite. The TCP/IP protocol suite also can be viewed as a set of layers. For example, the TCP/IP model can include five layers including an application layer, transport layer, internet layer, data link layer, and physical layer.

The computing device of the present disclosure can also include a firewall. A firewall can be used to control traffic between computer networks with different zones of trust. For example, the internet can be a zone with no trust and an internal network can be a zone with high trust. The goal is to provide controlled interfaces between zones of different trust levels through the enforcement of a security policy and connectivity model. In such embodiments, the encrypted bundled file can pass through the firewall to the internet connection using the Push model, as discussed herein.

In some embodiments, the computing device can receive instructions that are executable by the processor to export the encrypted bundled file to the storage computing system from a user of the computing device. In various embodiments, the computing device can include instructions executable by the processor to export the encrypted bundled file from the computing device to the storage computing system after the case study file has been in the computing device memory for a predetermined time. For example, if the case study file has been stored in the computing device memory for seven (7) days, the computing device can include instructions to export the case study file to the storage computing device automatically.

In some embodiments, the computing device can include instructions executable by the processor to allow changes to be made to the case study, which can be comprised of one or more case study files of any type or format. The changes can include adding an additional image file from the imaging modalities, adding a document, and/or making an edit to an existing document in the case study file. In various embodiments, instructions executable by the processor can monitor the imaging modalities for the additional image files to add to the case study. In such embodiments, the computing device can add the additional image files to the case study automatically once the imaging modality has completed its imaging. This can help to ensure that the case study includes all image files as well as the most recent image files.

In some embodiments, the computing device can include instructions executed by the processor to receive a case study file from the storage computing system in an encrypted form and the corresponding key used to encrypt the file. The computing device can then decrypt the stored file. As discussed herein, the case study file can be decrypted using a private key or a combination of a public key and a private key. In some embodiments, a symmetric key can be created and sent to the computing device using public-key encryption.

The computing device can also expand the stored file using a decompression routine, to obtain the original medical data file. The decompression routine can be stored in the memory of the computing device, or it can be sent to the computing device with the case study file.

In some embodiments, the computing device can include instructions executed by the processor to apply the case study file hash key to the expanded medical data file to ensure an accurate data transfer from the storage computing system. As discussed herein, if the stored medical data file within the stored case study file is altered or corrupted, a hash value found using the hash key, or hash function, will not equal the hash value of the case study file when the hash algorithm was originally performed on the medical data file.

In some embodiments, the computing device can include instructions executed by the processor to grant access rights to the case study file transferred to the storage computing system to one or more predetermined users. In addition, the storage computing system can store case study files from other computing devices, where the other computing devices have granted access rights to the stored case study files to one or more predetermined users. In such embodiments, the computing device and/or the other computing devices can include instructions executed by the processor to poll the storage computing system to check whether there are one or more stored case studies for the computing device and/or other computing devices to receive. Also, the storage computing system can send a message to the computing device and/or other computing devices indicating at least one study is available to be retrieved from the storage computing system.

In some embodiments, the storage computing device can include updates to the case study file. For example, the computing device can send the case study file to the storage computing device while designating a predetermined user.

The computing device of the predetermined user can then retrieve the case study file and make updates to the case study file. Further, the predetermined user can send the updated case study file to the storage computing device while designating the original user of the computing device. In such embodiments, the computing device can include instructions executable by the processor to update the case study file with information received from the storage computing system. The case study file stored on the computing device can either be updated by receiving only the changes to the case study file and merging the changes with the case study file or the entire case study file can be replaced with the updated case study file. As discussed herein, a case study is deemed modified when one or more of its associated case study files is added, modified, or deleted.

In some embodiments, records of changes and updates made to a case study file and/or a case study can be made to implement audit trails. With this, a history of data additions, updates, merges, and/or deletions can be referenced and/or generated for distribution. For enhanced applications, users might be associated to each of the data alterations, as well as the date and time the alterations were executed.

The storage computing device of the present disclosure can include processor and memory resources, as discussed herein. The memory can be coupled to the processor and contain executable instructions stored thereon that are executable by the processor to perform a method.

Figure 4:
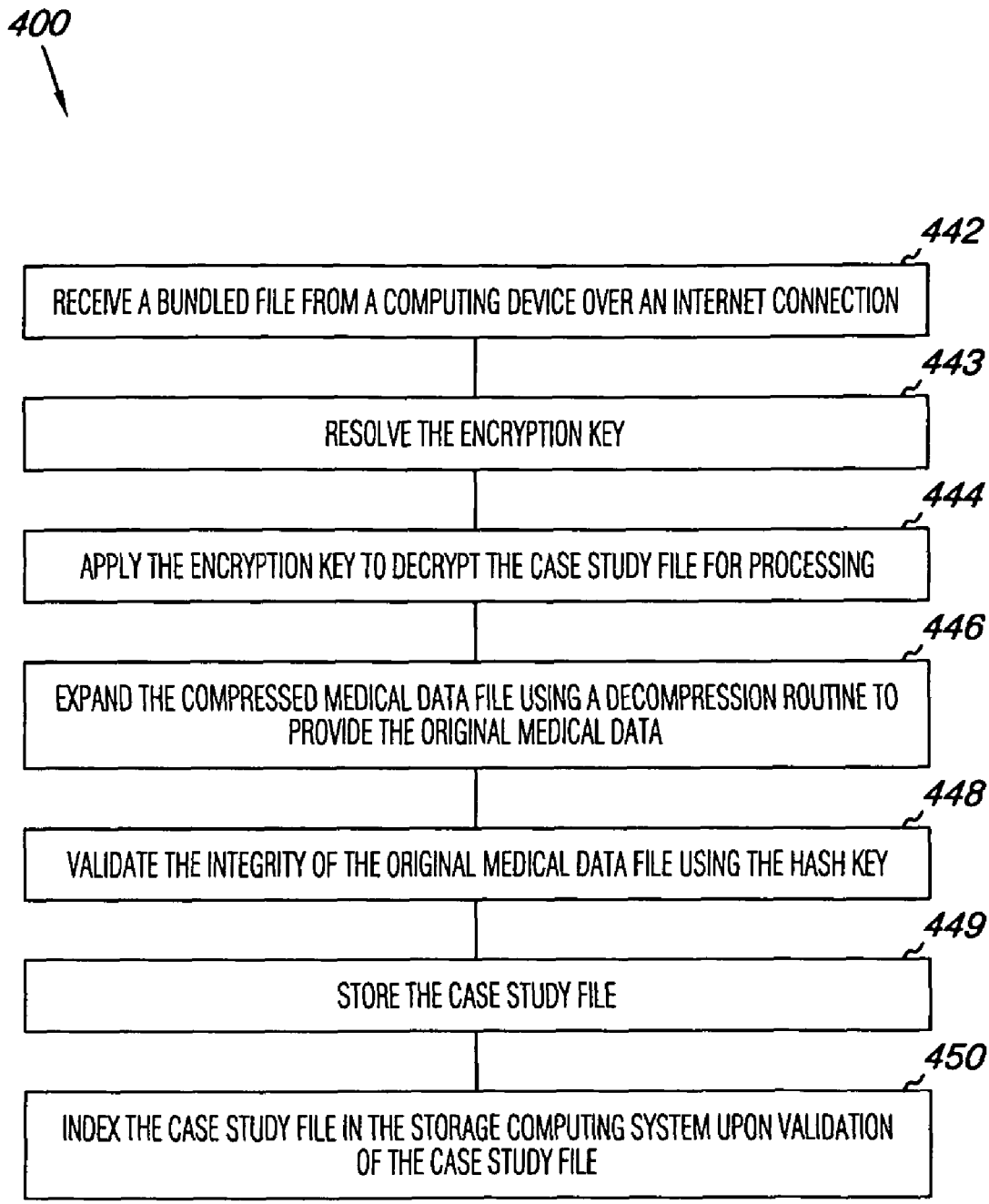
FIG. 4 illustrates a method for receiving and indexing a case study file in accordance with one or more embodiments of the present disclosure.

FIG. 4 illustrates a method for receiving and indexing a case study file according to embodiments of the present disclosure. As illustrated at block 442, the method 400 includes receiving a bundled file from a computing device over an internet connection. The bundled file, as discussed herein, can include a medical data file and a hash key to the case study file. In addition, the bundled file is in a compressed and encrypted form, as discussed herein.

As illustrated at block 443, a key used to encrypt a case study file, e.g., the encryption key, is resolved. In some embodiments, the encryption key can be provided to the remote storage computing system using Transport Layer Security (TLS), Secure Sockets Layer, or other cryptographic protocols applied to a network connection. In other embodiments in which an encrypted stream may not be feasible, the encryption key can be encrypted prior to transmission using a symmetric key model where a unique key is installed on both the transmitting and receiving systems.

At block 444, the encryption key is applied to decrypt the case study file for processing. This produces, among other elements, a hash key for the original medical data file and the compressed medical data file. As shown at block 446, the storage computing device expands the compressed medical data file using a decompression routine to provide the original medical data.

At block 448, the instructions stored on the memory of the storage computing device and executable by the processor validate the integrity of the original medical data file using the hash key. As discussed herein, the hash algorithm can be executed on the uncompressed medical data file or, in some embodiments, the compressed medical data file. If the hash key, based on the hash value, calculated by the storage computing device differs from the hash key sent with the case study file, it is an indication that an error has occurred at some point during the transmission. The error could be that a file has been altered, that information is missing from a file, and/or that an error occurred during compression and/or encryption, among other errors.

At block 449, the receiving entity stores the case study file. In some embodiments, the receiving entity may store the case study file in its native, e.g., uncompressed, unencrypted, format. In other embodiments, the receiving entity may store the case study file in a bundled, encrypted format. In such embodiments, the encryption key is itself encrypted with a key installed only on the receiving system, and then the key is stored and associated with the case study file to allow for future decryption or transfer requests.

As shown at block 450, the storage computing system can index the case study file in the storage computing system upon validation of the case study file. In some embodiments, the storage computing system can index the case study file according to the sender of the bundled file. For example, when a computing device from a particular facility sends the bundled file to the storage computing system, the storage computing system can index it with other bundled or unbundled files from the facility. The storage computing device can then further index the bundled file according to the treatment professional, the patient, and/or the size of the bundled files, among other criterion.

In some embodiments, instructions stored on the memory and executable by the processor can make a billing entry in the storage computing system for the case study file. In some embodiments, the billing entry can be a flat fee charged for the case study file. In various embodiments, the billing entry can depend on the size of the case study file, the types of image files in the case study file, and/or the number of case study files that have been sent for a particular patient.

In some embodiments, the storage computing system can note the number of files included in the case study and group the number of files according to their type. For example, the number of MRI images can be noted, the number of ultrasounds images can be noted, etc. The storage computing system includes instructions executable by the processor to generate an invoice indicating a case study fee, as discussed herein, and/or a fee for the number of files in the case study. In some embodiments, the storage computing system can include instructions executable by the process to allow a user to access and view the invoice.

In some embodiments, the fee for the number of files can employ a sliding scale. In other words, a first file of a first type can be priced higher than a second file of the first type. For example, a first MRI image can have a fee of two dollars ($2.00), and a second MRI image can have a fee of fifty cents ($0.50).

In some embodiments, the case study file fee can also employ a sliding scale for a particular patient. In other words, a first case study file including a first medical data file and a second case study file including a second medical data file can be received by the storage computing device over the internet connection. However, the first case study file and the second case study file can be for the same patient. In such embodiments, the case study file fee for the first case study file can be a first amount and the case study file fee for the second case study file can be a second amount. For example, the first case study file can include a medical data file for the patient, John Doe. The second case study file can include a second medical data file also for the patient, John Doe. The case study file fee can be twenty dollars ($20.00) for the first case study file for John Doe and the case study file fee can be five dollars ($5.00) for the second case study file for John Doe. In some embodiments, the case study file fee is the second amount (e.g., five dollars ($5.00)) for a predetermined amount of time (e.g., 24 hours).

As discussed herein, in some embodiments, a bundled or case study file can include the medical data file and the hash key. In addition, the case study file can include a list of one or more predetermined users. The one or more predetermined users are allowed to access the bundled file. As such, in some embodiments, the storage computing system can receive a request over the internet connection from the computing device for access to the case study file stored on the storage computing system.

When the storage computing system receives the request, the storage computing system can verify authorization for the request to access the case study file. For example, the storage computing system can check the list of one or more predetermined users, which can be based on an IP address or Media Access Control (MAC) address. The storage computing system can also have a username and password system in place, where a user enters the username and password, and the storage computing system verifies if that username and password combination have been granted access to a case study file based on the list of one or more predetermined users. The system can also have other elements to limit and control access to case study files and associated data, as will be appreciated by one of ordinary skill in the art.

Once the authorization for the request has been verified, instructions executable by the processor can access the case study file, execute the processes previously discussed in connection with FIG. 3 if the file is stored in its native format rather than the bundled format, as discussed herein, and send the bundled case study file through the internet or other network connection to the requesting computing device.

As discussed herein, in some embodiments, the case study can be updated or changed by the computing device that created the case study file when, for example, an additional file is created or acquired. In some embodiments, the case study can be updated after it has been received by the storage computing system. In such embodiments, instructions executable by the processor in the storage computing system can update the case study when the storage computing system receives, for example, an additional case study file associated with the case study, from the computing device.

In some embodiments, the storage computing system can receive a bundled case study file from a first computing device over the internet or other network connection. The storage computing system can then decrypt and decompress the bundled file to provide the medical data file and the hash key. The storage computing system can further include instructions executable by the processor to validate the integrity of the medical data file using the hash key and index the case study file upon validation.

In some embodiments, the storage computing system can also indicate to an approved computing device the existence of the case study associated with the received case study file. As used herein, an "approved computing device" can refer to a specific computing device, where the computing device has been identified as an approved computing device by the device's IP address, MAC address, or other element unique to the device. The "approved computing device" can also refer to the computing device that is being used by an approved user or facility. In some embodiments, the approved user can be validated by a username and password.

In embodiments where the storage computing device employs usernames and passwords to allow for the sending and retrieving of bundled files, the storage computing device can associate the approved user and the creating user with the bundled file when the bundled file is received by the storage computing system from the computing device. As used herein, the "creating user" refers to the user who initially initiates the sending of a case study file to the storage computing system from one of the number of computing devices.

As discussed herein, the storage computing system can receive a list of one or more predetermined users with the case study file. In some embodiments, the storage computing system can include instructions executable by the processor to provide a list of users, and the computing device user can identify specific users who can access the case study file. In some embodiments, groups of users may be granted access to the case study file, such as all approved members within a specific facility. Other methods of identifying approved users are also possible.

In some embodiments, the storage computing system can indicate to the approved computing device the existence of the case study file by sending a notice to the approved computing device. For example, the storage computing system can send an electronic mail message to an electronic mail account of an approved user, and the approved user can access the electronic mail message using a computing device. In various embodiments, the storage computing system can indicate to the approved computing device the existence of the case study file by sending the electronic mail message to the approved computing device itself, or by notifying the device directly through a network connection and a responding application.

In some embodiments, the storage computing system can indicate to the approved computing device the existence of the case study file by executing to flag the approved computing device in a list of the number of computing devices stored in the storage computing system. In such embodiments, the storage computing device can include instructions executable by the processor to receive a query from the number of computing devices to determine whether at least one of the number of computing devices has been flagged as an approved computing device.

The storage computing device can also include instructions executable by the processor to receive a request over the internet connection from at least one of the first computing device or a second computing device for access to the case study file stored on the storage computing system. In some embodiments, the first computing device can send the storage computing device the case study file and then erase the case study file from the first computing device memory. In such embodiments, if a user of the first computing device would like to view the case study file, the first computing device can send a request to the storage computing device for access.

The storage computing device can then verify that at least one of the first computing device or the second computing device is the approved computing device, execute the processes previously discussed in connection with FIG. 3 if the medical data file is stored in its native format, and send the bundled case study file through the internet connection or other network connection to the approved computing device over the internet connection.

As discussed herein, in some embodiments, the number of computing devices can receive additional image files from the imaging modalities, an additional document file, and/or alterations to existing medical data files in the case study after the pertinent case study files have been sent to the storage computing device from the computing device. In such embodiments, the number of computing devices can send, and the storage computing device can receive, one or more of the additional case study file, additional document, and/or modifications to the medical data file in the case study file.

In some embodiments, new or modified case study files can be sent by the number of computing devices automatically. For example, the first computing device can send the case study file to the storage computing facility. However, an additional file is received by the first computing device from the imaging modality after the case study file has been sent. In such embodiments, the first computing device can include instructions executable by the processor to identify the image file as an additional image file for the case study, and send the additional file to the storage computing system. Subsequently, the additional image file can include a case study identifier, so that the storage computing system can add the additional image file to the appropriate case study after the additional image file is received.

In some embodiments, the updates to the case study can be sent by the number of computer devices to the storage computing device after a user initiates a send request on at least one of the number of computing devices. In various embodiments, the updates to the case study file can be sent by the number of computing devices to the storage computing device automatically, as discussed herein, as well as after the initiation of a send request.

Once the updates to the case study have been received by the storage computing device and added to the case study file stored on the storage computing system, the storage computing system can indicate to the approved computing device the existence of the additional image file from the imaging modality, the additional document file, and/or edits to the document file in the case study file. In some embodiments, the storage computing system can indicate the update to the case study by sending a notice to the approved computing device, as discussed herein. Also, in various embodiments, the storage computing system can indicate the update to the case study by flagging the approved computing device in a list of computing devices stored in the storage computing system, as discussed herein.

In some embodiments, after a second computing device, or approved computing device, has received the case study file, the second computing device can also send an additional image file, additional document file, and/or edits to the file in the case study to the storage computing system to update the case study. In such embodiments, the second computing device can send the updates alone or the entire case study file including the updates. As such, the storage computing device can include instructions executable by the processor to merge the updates with the stored case study file, add the updates to the stored case study while also keeping the updates separate from the pertinent case study file, replace the stored case study file with the updated case study file, or save the updated case study file separate from the case study file.

In some embodiments, once the storage computing device has received the updates to the case study, the storage computing device can include instructions to indicate to the first computing device, or creating user, the existence of the updates to the case study, as discussed herein with respect to indicating the existence of the case study file or files to the one or more predetermined users, or approved computing device.

Embodiments of the present disclosure can also be used as a method of case study file management. As discussed herein, the storage computing device can receive the bundled file from the computing device over the internet or other network connection, decrypt the bundled file, validate the integrity of the included medical data file, and index the case study file upon validation. Further, the storage computing device can receive updates to the case study file from the computing device.

The method can also include saving the bundled file, including the case study file, hash key, and/or updates to the case study file to a computing device readable medium after a predetermined time interval. For example, a particular clinic can have a business practice of sending the case study files as bundled files to the storage computing system as a backup storage system. In addition, the bundled files can be saved to, for example, portable media and sent to the particular clinic every month, or every year, depending on the volume of bundled files generated by the particular clinic. The media can then be kept at the particular clinic or at a third secure storage site.

As discussed herein, methods of the present disclosure can include billing the users for the storage of the bundled files, as well as for other services provided. In addition, in some embodiments, the particular clinic that receives the bundled files on a computing device readable medium can also be billed. The billing can include the cost of shipping and/or the cost of the computing device readable medium itself.

Figure 5:
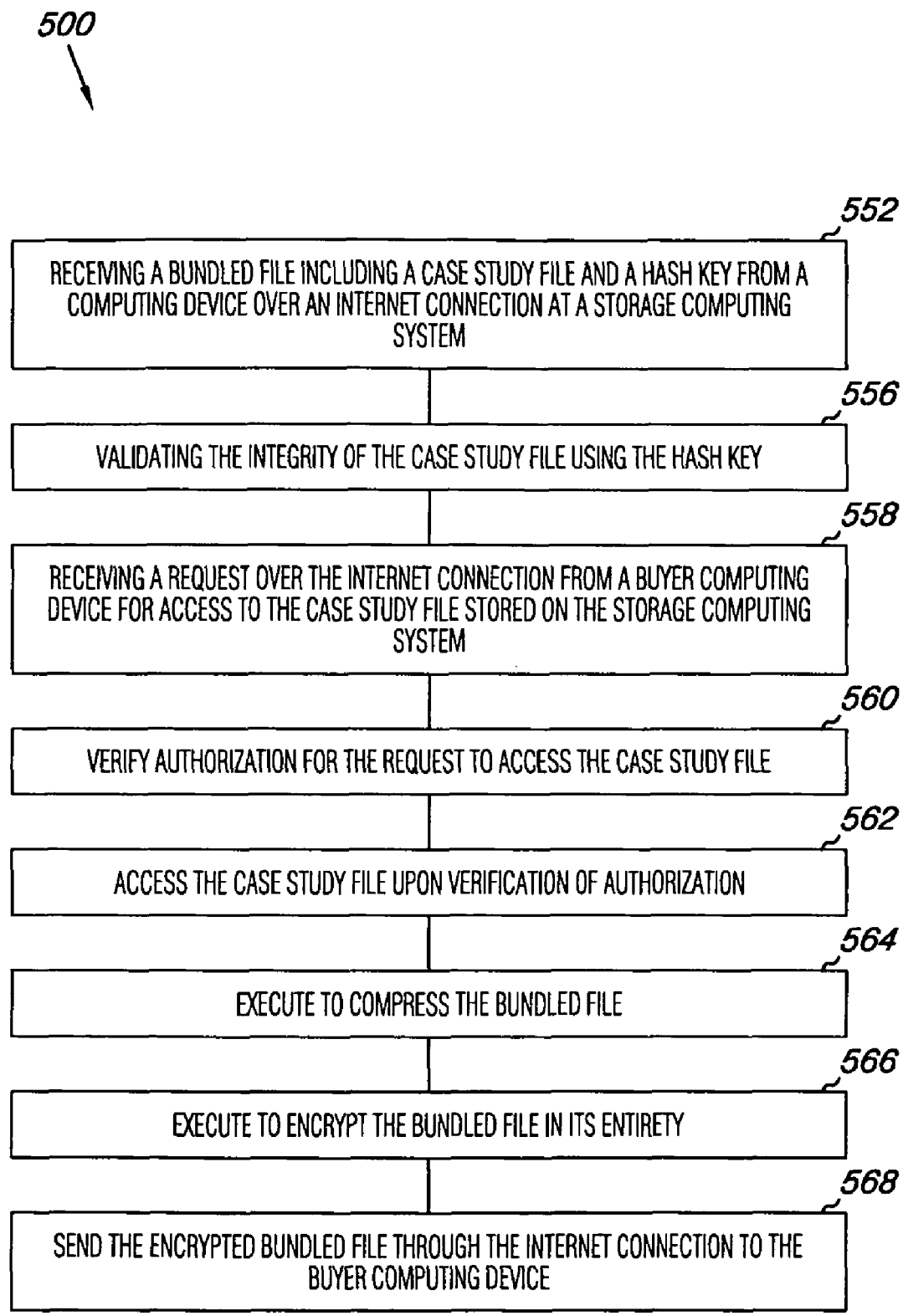
FIG. 5 illustrates a method for selling an animal in accordance with one or more embodiments of the present disclosure.

FIG. 5 illustrates a method for selling an animal according to embodiments of the present disclosure. As illustrated at block 552, the method 500 includes receiving the bundled file including the case study file and the hash key from the computing device over an internet connection at the storage computing system, as discussed herein. In some embodiments, the internet connection can be an unsecure internet connection, as discussed herein.

The case study file can include a number of images of the animal, including photographs, x-rays, MRIs, and ultrasounds, among others. The images can be taken of the entire animal body as well as portions of the body. Also, at block 556, the integrity of the case study file can be validated using the hash key, as discussed herein.

As illustrated at block 558, the method 500 includes receiving a request at the storage computing system over the internet connection from a buyer computing device for access to the case study file stored on the storage computing system. Subsequently, the authorization for the request to access the case study file is verified, as shown at block 560. The authorization for the request to access the case study file can be verified in a number of ways. In some embodiments, a potential buyer can contact the seller to express an interest in the animal. The seller can then contact the storage computing system by sending a request to add the potential buyer to a list of authorized users to access the case study file. The storage computing device can then send a username and password to the buyer computing device. The potential buyer can then enter the username and password at a storage computing device prompt. Upon the entering of a valid username and password, the storage computing device has verified authorization for the request to access the case study file.

In some embodiments, a seller can provide a list of one or more predetermined authorized users with the case study file. The predetermined authorized users can be identified by a unique computing device IP address and/or using a username and password combination, as discussed herein.

At block 562 the storage computing device can access the case study file upon verification of authorization. The storage computing device can then execute to compress the bundled file, encrypt the bundled file in its entirety, and send the encrypted bundled files through the internet connection to the buyer computing device, as shown at blocks 564, 566, and 568, respectively.

In some embodiments, once the buyer computing device has received the bundled file from the storage computing device, the buyer computing device can decrypt the bundled file, expand the bundled file to provide the case study file and the hash key, and validate the integrity of the case study file using the hash key, as discussed herein.

In some embodiments, the method of selling the animal can include making the case study file available for a predetermined time interval. For example, the seller can set a specified time for potential buyers to arrange for a username and password (e.g., seven (7) days), and can then set a specified time for the potential buyers to review the case study file (e.g., fourteen (14) days).

What is claimed:

1. A computing device, comprising:
   a processor;
   a memory coupled to the processor, the memory having executable instructions stored thereon that are executable by the processor to:
   create a case study file that includes an image file from an imaging modality;
   execute a hash algorithm on the image file of the case study file to produce a hash key placed in the case study file to produce a bundled file;
   execute to compress the bundled file;
   execute to encrypt the bundled file in its entirety;
   make an outbound request to move the encrypted bundled file through an internet connection to a storage computing system in communication with the computing device over the internet connection;
   indicate to an approved computing device the existence of the case study file and flag the approved computing device in a list of a number of computing devices stored in the storage computing system; and
   receive a query from the number of computing devices to determine whether at least one of the number of computing devices has been flagged as an approved computing device.

2. The computing device of claim 1, where the outbound request moves the encrypted bundled file through an unsecure internet connection to the storage system.

3. The computing device of claim 1, where the executable instructions are executable by the processor to allow changes to be made to the case study file.

4. The computing device of claim 3, where changes to the case study file include adding one or more of an additional image file from the imaging modality, a document, and edits to an existing document in the case study file.

5. The computing device of claim 1, where the encrypted bundled file is transferred through the internet using IP protocol.

6. The computing device of claim 1, where the executable instructions are executed by the processor to poll the storage computing system to check whether there are one or more studies for the computing device to receive and where the storage computing system sends a message to the computing device indicating at least one study available to be retrieved from the storage system.

7. The computing device of claim 1, where the executable instructions are executed by the processor to:
   receive a stored file containing a stored case study from the storage computing system in an encrypted form and a stored file hash key;
   decrypt the stored file;
   decompress the stored file; and
   apply the stored file hash key to the stored case study and a stored file image file to ensure a lossless data transfer from the storage computing system.

8. The computing device of claim 1, where executable instructions are executed by the processor to grant access rights to the case study file in the storage computing system to one or more predetermined users.

9. The computing device of claim 8, where executable instructions on computing devices of the one or more predetermined users execute on one or more processors to poll the storage computing system for one or more stored case study files having access rights granted by an additional computing device.

10. The computing device of claim 1, where the executable instructions are executed by the processor to provide lossless compression to the bundled file.

11. The computing device of claim 1, where the computing device includes a firewall, and where the encrypted bundled file passes through the firewall to the internet connection.

12. The computing device of claim 1, where the executable instructions are executed by the processor to receive instructions from a user of the computing device to export the encrypted bundled file.

13. The computing device of claim 1, where the executable instructions are executed by the processor to monitor the image modalities for additional image files to add to the case study file.

14. The computing device of claim 1, where the executable instructions are executed by the processor to update the case study file with information received from the storage computing system in communication with the computing device over the internet connection.

15. The computing device of claim 1, where the image file is in a DICOM format.

16. The computing device of claim 1, where the case study file includes document files.

17. A storage computing system, comprising:
   a processor;
   a memory coupled to the processor, the memory having executable instructions stored thereon that are executable by the processor to:
   receive a bundled file from a computing device over an internet connection, where the bundled file is in a compressed and an encrypted form;
   decrypt the bundled file;
   decompress the bundled file to provide a case study file and a hash key to the case study file;
   validate the integrity of the case study file using the hash key;
   index the case study file in the storage computing system upon validation of the case study file;
   receive updates to the case study file from the computing device;
   save the bundled file including the case study file, the hash key, and updates to the case study file to a computing device readable medium after a predetermined time interval; and
   send the computing device readable medium to a clinic.

18. The storage computing system of claim 17, where the bundled file is received over an unsecure internet connection.

19. The storage computing system of claim 17, where the executable instructions are executable by the processor to make a billing entry in the storage computing system for the case study file.

20. The storage computing system of claim 17, where the executable instructions are executable by the processor to:
   receive a request over the internet connection from the computing device for access to the case study file stored on the storage computing system;
   verify authorization for the request to access the case study file;
   access the case study file upon verification of authorization;
   execute to recompress the bundled file;
   execute to re-encrypt the bundled file in its entirety; and send the re-encrypted bundled file through the internet connection to the computing device over the internet connection.

21. The storage computing system of claim 17, where the executable instructions are executable by the processor to update the case study file received in the bundled file in the storage computing system.

22. A system, comprising:
a storage computing system and a number of computing devices, where the storage computing system and the number of computing devices include:
a processor;
a memory coupled to the processor, the memory having executable instructions stored thereon that are executable by the processor to:
receive a bundled file from a first computing device over an internet connection, where the bundled file is in a compressed and an encrypted form;
decrypt and decompress the bundled file to provide a case study file and a hash key to the case study file;
validate the integrity of the case study file using the hash key;
index the case study file in the storage computing system upon validation of the case study file;
indicate to an approved computing device the existence of the case study file and flag the approved computing device in a list of the number of computing devices stored in the storage computing system;
receive a query from the number of computing devices to determine whether at least one of the number of computing devices has been flagged as an approved computing device;
receive a request over the internet connection from at least one of the first computing device or a second computing device for access to the case study file stored on the storage computing system;
verify that at least one of the first computing device or the second computing device is the approved computing device;
execute to recompress and re-encrypt the bundled file in its entirety; and
send the re-encrypted bundled file through the internet connection to the approved computing device over the internet connection.

23. The system of claim 22, where the executable instructions executable by the processor to indicate to an approved computing device the existence of the case study file execute to send a notice to the approved computing device.

24. The system of claim 22, where the case study file contains an image file from an imaging modality and a document file, and where executable instructions are executable by the processor to receive one or more of an additional image file from the imaging modality, an additional document file, and edits to the document file in the case study file.

25. The system of claim 24, where one or more of the additional image file from the imaging modality, the additional document file, and edits to the document file in the case study are sent by the number of computing devices automatically.

26. The system of claim 24, where one or more of the additional image file from the imaging modality, the additional document file, and edits to the document file in the case study are sent by the number of computing devices after a user initiates a send request on at least one of the number of computing devices.

27. The system of claim 24, where one or more of the additional image file from the imaging modality, the additional document file, and edits to the document file in the case study are sent by the number of computing devices automatically and after a user initiates a send request on at least one of the number of computing devices.

28. The system of claim 24, where the executable instructions executable by the processor are executed to add the one or more additional image file from the imaging modality, the additional document file, and edits to the document file in the case study file to the case study file.

29. The system of claim 28, where executable instructions are executed by the processor to indicate to the approved computing device the existence of the one or more additional image file from the imaging modality, the additional document file, and edits to the document file in the case study file.

30. The system of claim 29, where the executable instructions executable by the processor to indicate to the approved computing device the existence of the one or more additional image file from the imaging modality, the additional document file, and edits to the document file in the case study file executes to send a notice to the approved computing device.

31. The system of claim 29, where the executable instructions executable by the processor to indicate to the approved computing device the existence of the one or more additional image file from the imaging modality, the additional document file, and edits to the document file in the case study file executes to flag the approved computing device in a list of the number of computing devices stored in the storage computing system.

32. A method, comprising:
creating a case study file, including an image file from an imaging modality on a computing device;
executing a hash algorithm on the image file of the case study file to produce a hash key;
producing a bundled file including the case study file and the hash key;
compressing the bundled file;
encrypting the bundled file in its entirety;
sending the encrypted bundled file through an internet connection to a storage computing system in communication with the computing device;
receiving updates to the case study file from the computing device;
saving the bundled file including the case study file, the hash key, and updates to the case study file to a computing device readable medium after a predetermined time interval; and
sending the computing device readable medium to a clinic.

33. The method of claim 32, where the method includes associating an approved user and a creating user with the bundled file.

34. The method of claim 33, where the method includes indicating to the approved user the existence of the case study file.

35. The method of claim 34, where the method includes sending the case study file from the storage computing system to a computing device of the approved user.

36. The method of claim 35, where the method includes sending one or more of an additional image file, an additional document file, and edits to a document file in the case study file from the computing device of the approved user to the storage computing system to be added to the case study file.

37. The method of claim 36, where the method includes indicating to the creating user the existence of one or more of the additional image file, the additional document file, and edits to the document file in the case study file.

38. The method of claim 32, where the internet connection is an unsecured internet connection.

39. The method of claim 32, including updating the case study file by sending one or more of an additional image file from the imaging modality, an additional document file, and edits to a document file in the case study file from the computing device to the storage computing system.

40. A method of case study file management, comprising:

receiving a bundled file from a computing device over an internet connection, where the bundled file includes a case study file and a hash key in a compressed and encrypted form;

decrypting the bundled file and validating the integrity of the case study file using the hash key;

indexing the case study file in a storage computing system upon validation of the case study file;

receiving updates to the case study file from the computing device;

saving the bundled file including the case study file, the hash key, and updates to the case study file to a computing device readable medium after a predetermined time interval; and sending the computing device readable medium to a clinic.

* * * * *